United States Patent [19]

Gemmell et al.

[11] Patent Number: 4,979,094
[45] Date of Patent: Dec. 18, 1990

[54] CONTROL SYSTEM

[75] Inventors: David Gemmell, Sutton; Duncan A. Irvine, Aylesbury, both of United Kingdom

[73] Assignee: Possum Controls Limited, Buckinghamshire, United Kingdom

[21] Appl. No.: 176,882

[22] Filed: Apr. 4, 1988

[30] Foreign Application Priority Data

Apr. 7, 1987 [GB] United Kingdom ................. 8708314
Feb. 24, 1988 [GB] United Kingdom ................. 8804331

[51] Int. Cl.$^5$ .......................... G06F 15/20; H04Q 9/00
[52] U.S. Cl. .................................... 364/188; 364/146; 340/825.19
[58] Field of Search ............................... 364/131–133, 364/138, 139, 143, 145, 146, 188, 189, 401, 410; 340/825.06, 825.22, 310 A, 310 CP, 286 R, 825.19

[56] References Cited

U.S. PATENT DOCUMENTS 3,241,115  3/1966  Maling ............................... 340/147
3,771,156  11/1973  Watts et al. ........................ 340/325
3,781,802  12/1972  Kafafian .......................... 340/147 R (List continued on next page.)

FOREIGN PATENT DOCUMENTS 2803599 of 1978 Fed. Rep. of Germany.
660956A  6/1987 Switzerland.

(List continued on next page.)

OTHER PUBLICATIONS

*Possum Selector Unit–Type 1 Instruction Manual*, Possum Controls Limited, for the PSU1 and PSU1 with Servophone (LST5B); Mar. 1973.
*System 7 "The Remote Display" and Users' Manual* Zambette Electronics, Ltd.
*Possum PSU 3 Environmental Control System, User's Handbook*, Possum Controls Ltd.
"Typewriter for the Disabled" Techlink Unit, Technology Reports Centre Techlink No. 1474, Department of Trade and Industry, 1974.

"Interactive Graphics Applied to Symbol–Communication for Non-Speaking Children", *Computers and Graphics*, vol. 2, No. 4, 1977, pp. 201–204.
"Conference Proceedings on Communications", Eurocon 1977, May 3–7, 1977, Venice, Italy, Conference on Electrotechnics.
*Byte*, Sep. 1982, vol. 7, No. 9, "Computers and the Disabled".
*Computer*, vol. 14, No. 1, Jan. 1981, articles referring to Computing and the Handicapped.
"Wombat User's Reference Manual", and Possum Text Processor Leaflet, pp. A-1 though A-3.
The Micro Enquirer BBC Micro, pp. 76 to 80 and 123 to 124.
8079 Electro/81 Conference Record pp. 1–10, vol. 6, (1981) Apr. 7–9, New York, NY, USA.

*Primary Examiner*—Jerry Smith
*Assistant Examiner*—Paul Gordon
*Attorney, Agent, or Firm*—Robert F. O'Connell

[57] ABSTRACT

Control apparatus is provided having a microprocessor-based control unit which includes EPROM stored programs for controlling two input stations, loudspeaking telephones, and a plurality of switching devices included on a serial link with the input stations. Each station has a television type monitor on the screen of which, when an input switching device, which is operable by a disabled person, is actuated, a main menu is presented in the form of a list of those of the devices and the telephones which can be controlled from that station. By use of the input switching device and the menu display, a device or the telephone can be selected for control. If control involves more than power on or off, a new menu appears listing the various functions to be chosen, e.g. television channel, volume control. The menus are presented in color determined on a pixel-by-pixel basis. Each switching device controls the operation of a domestic appliance such as an electric fire, lamp, radio or television and also has a manually operable push button and the control unit detects actuation of the push button and in response causes the switching device to change the state of the associated appliance from ON to OFF or vice versa.

5 Claims, 13 Drawing Sheets

U.S. PATENT DOCUMENTS

| | | | |
|---|---|---|---|
| 3,818,448 | 6/1974 | Wilkins | 340/147 R |
| 3,848,249 | 11/1974 | Meiri | 340/286 E |
| 3,911,316 | 10/1975 | Feick et al. | 318/562 |
| 4,001,801 | 1/1977 | Dallimonti | 364/189 |
| 4,086,434 | 4/1978 | Bocchi | 179/2 AM |
| 4,183,015 | 1/1980 | Drew et al. | 340/286 R |
| 4,237,344 | 12/1980 | Moore | 340/286 R |
| 4,241,521 | 12/1980 | Dufresne | 434/112 |
| 4,279,012 | 7/1981 | Beckedorff et al. | 364/146 |
| 4,338,493 | 7/1982 | Stenhuis et al. | 179/5 R |
| 4,415,065 | 11/1983 | Sandstedt | 364/401 |
| 4,418,333 | 11/1983 | Schwarzbach et al. | 364/146 |
| 4,430,639 | 2/1984 | Bennett | 340/310 A |
| 4,547,851 | 10/1985 | Kurland | 364/410 |
| 4,558,315 | 12/1985 | Weiss et al. | 340/802 |
| 4,703,306 | 10/1987 | Baritt | 340/310 CP |
| 4,843,386 | 6/1989 | Wolf | 340/825.06 |

FOREIGN PATENT DOCUMENTS

| | | |
|---|---|---|
| 1021531 | 5/1962 | United Kingdom . |
| 956302 | 2/1963 | United Kingdom . |
| 1439591 | 3/1972 | United Kingdom . |
| 1417849 | 12/1972 | United Kingdom . |
| 1417850 | 12/1972 | United Kingdom . |
| 1459902 | 2/1974 | United Kingdom . |
| 1468579 | 4/1974 | United Kingdom . |
| 2013955 | 1/1979 | United Kingdom . |
| 2056729B | 7/1980 | United Kingdom . |
| 2058419A | 9/1980 | United Kingdom . |
| 2128386A | 10/1982 | United Kingdom . |
| 2128786A | 10/1982 | United Kingdom . |
| 2137001A | 3/1983 | United Kingdom . |
| 2166627 | 3/1983 | United Kingdom . |
| 2145257A | 7/1983 | United Kingdom . |
| 2136617A | 3/1984 | United Kingdom . |
| WO8100478 | 9/1980 | World Int. Prop. O. . |

| | |
|---|---|
| START | |
| ALARM | |
| SEIZE LINE | |
| INTERCOM | |
| TELEPHONE | |
| COMMUNICATIONS | TAPE RECORDER |
| BED | RADIO |
| SOCKETS #1 | TELEVISION |

*FIG. 2*

| | |
|---|---|
| START | |
| RESET | |
| DOOR 1 | |
| DOOR 2 | |
| INTERCOM 1 | CALL 4 |
| INTERCOM 2 | CALL 3 |
| INTERCOM 3 | CALL 2 |
| INTERCOM 4 | CALL 1 |

*FIG. 3*

| | |
|---|---|
| START | |
| RESET | |
| SKT 01 FAN | |
| SKT 02 HEATER | |
| SKT 03 LAMP | |
| SKT 04 BLANKET | |
| SKT 05 | |
| SKT 06 | SKT 07 |

*FIG. 4*

| | |
|---|---|
| START | A7 SOCIAL SERVICES |
| RESET | A6 MEALS ON WHEELS |
| SIEZE LINE  # # | A5 DUNCAN IRVINE |
| DIAL OUT | A4 TERRY ALEXANDER |
| HIGH VOLUME  # # | A3 WARDEN'S FLAT |
| NEXT PAGE (B1-B8) | A2 POSSUM CONTROLS |
| SET UP NUMBER | A1 OPERATOR |
| SET UP NAME | TS |

FIG.5

| | |
|---|---|
| START | ENTER NUMBER |
| RESET | RESUME EDITING |
| 0 | DELETE |
| 1 | HYPHEN |
| 2 | 9 |
| 3 | 8 |
| 4 | 7 |
| 5 | 6 |

FIG.6

| | SPC | D/C | D/L | R/E | ENT | | |
|---|---|---|---|---|---|---|---|
| RST | E | . | . | | | | |
| T | O | S | L | Y | X | , | / |
| A | R | M | D | V | & | ) | ! |
| N | H | C | B | J | ( | ; | : |
| I | F | W | Z | - | = | | + |
| U | P | Q | 0 | 1 | 2 | 3 | 4 |
| G | K | ? | 5 | 6 | 7 | 8 | 9 |

FIG.7

| | |
|---|---|
| START | |
| RESET | |
| TV OFF | |
| TV ON | CH7 |
| VOLUME UP | CH6 |
| VOLUME DOWN | CH5 |
| CH1 | CH4 |
| CH2 | CH3 |

FIG. 8

| | | SPC | D/C | D/L | | | | |
|---|---|---|---|---|---|---|---|---|
| RST | E | CR | 1/c | . | , | RPT | CMD |
| T | O | S | L | Y | X | ' | / |
| A | R | M | D | V | & | ) | ! |
| N | H | C | B | J | ( | ; | : |
| I | F | W | Z | – | = | * | + |
| U | P | Q | PND | < | > | # | ← |
| G | K | ? | @ | — | → | ↑ | $ |

FIG. 9

CONTROL SYSTEM

This invention relates to a control system for use by, for example, a disabled person.

For many years there have been available for severely physically disabled persons equipments known as environmental control systems in which a display provides the user with an indication of which one of a plurality of domestic appliances, for example a radio, an electric fire, a television, a telephone, a page turner and an alarm, is in operation under the control of the control system. Such a system may have input means in the form of one or two on/off switches, possibly adapted to be controlled by sucking and/or blowing by the user, the operations of the switch or switches being automatically responded to by the system to provide the user with a method of initiating, controlling and terminating a scanning of the display positions of the display. Examples of such equipment used in the United Kingdom are the environmental control systems known respectively as the PSU1 and PSU3 manufactured by Possum Controls Limited.

Another piece of equipment manufactured by Possum Controls Limited is a communicator for use by non-verbal severely disabled persons. The communicator has a panel of, for example, 10×10 cells mounted in a brief case type housing. The cells of the panel can be illuminated from behind by selectable light sources. Vertical, horizontal and diagonal scanning can be effected by selective sequential operations of the light sources. Transparent overlay sheets which slip into position in front of the panel are supplied with the communicator, each providing a set of words or phrases appropriate for particular circumstances. For example, four basic overlay sheets may relate respectively to general communication, food as in eating and shopping, clothes as in dressing and shopping, and a simple alphabet and symbol set. One such communicator, known as the Communicator 100, has a number of display cells associated with a memory facility so that phrases or sentences composed of words selected and stored in advance by the user by means of this facility can be displayed as a complete recalled expression.

Such communicator apparatus is provided with input means corresponding to the type of input means used with environmental control systems. A description of a micro-processor based communicator system is given in patent specification GB No. 2 058 419. A micro-processor based environmental control system is described in patent specification GB No. 2 137 001.

All of the apparatus mentioned specifically hereinbefore makes use of a display panel or area in which individual parts are illuminated by discrete light sources. Such display arrangements lack flexibility, and, in the case of the communicator, impose a distracting departure from the normal spatial arrangement of word sequences.

A microprocessor-based word processor adapted for use by severely physically disabled persons has also been produced, under the name WOMBAT, manufactured by Possum Control Limited, which utilizes a domestic television set for displaying words, phrases and complete texts. However, to control the operation of the WOMBAT, a separate display panel with selectable light sources is required.

It is an object of the present invention to provide an environmental control system for use by a disabled person, the control system having a controlled display which presents information on a television-type screen.

Another object of the invention is to provide an environmental control system capable of being actuated from a plurality of input stations, and each input station having a respective set of controlled outputs of the system associated therewith.

A further object of the invention is to provide digital video processing apparatus allowing a range of selectable colour data to be allocated to character data encoded by means of a relatively small number of bits.

Yet another object of the invention is to provide a power supply circuit which converts dc to dc with low output ripple and which can be constructed from relatively small valued components.

According to one aspect of the present invention, there is provided a control system for controlling a plurality of electrically operable switching devices, the system having a control unit coupled to the plurality of switching devices and to a plurality of input stations, each input station having an input device actuable by a user, and a visible display means for displaying information relating to the system, the control unit being adapted to effect control of the switching devices and the input stations in response to actuation of any one of said input devices and being such that information displayed at and input effected through any one of said input stations is restricted to information relating to and control of a predetermined group of said switching devices associated by said control unit with the said one input station.

According to another aspect of the invention there is provided display apparatus comprising means for presenting a television-type raster, means for storing at least one pixel map of the raster, and means for generating colour signals in response to each pixel of the pixel map, including means for storing a plurality of colour codes for each pixel of the pixel map, means for selecting one or another of each such plurality of colour codes in dependence upon a value stored for the respective pixel in the pixel map, and means for converting the selected colour code into a corresponding colour signal.

According to a further aspect of the invention there is provided a power supply circuit having a plurality of controlled switching means arranged to transfer input energy to magnetic energy storage means, the magnetic energy storage means being adapted to supply output energy, and means for so controlling conduction of current through the switching means that the switching means conduct in a cyclic sequence and are respectively conducting for a duration that is less than the duration of one complete cycle of the sequence.

According to yet a further aspect of the invention there is provided a power supply circuit having a current input terminal, a current output terminal, a plurality of switching means coupled in series with inductive means between the current input and output terminals, and means for so controlling conduction of current through the switching means that the switching means conduct in a cyclic sequence and are respectively conducting for a duration that is less than the duration of one complete cycle of the sequence.

According to another aspect of the invention there is provided a control system for controlling a plurality of electrically operable switching devices, the system having a control unit coupled to the plurality of switching devices and to at least one input station, the or each input station having an input device actuable by a disabled user and a visible display means for displaying information relating to the system, the control unit being adapted to effect control of the said plurality or a predetermined group of the switching devices in response to actuation of the or any one said input device, and at least one of the switching devices including manually operable means for signalling a request to the control unit to change a control state of the switching device, the control unit being adapted to sense the request and to so control the switching device as to effect the requested change.

A preferred embodiment of the system has a microprocessor-based control unit which includes EPROM stored programs for controlling two or more input stations, loudspeaking telephones, and a plurality of switching devices included on a serial link with the input stations. Each input station has a television type monitor on the screen of which, when an input switching device operable by a disabled person is actuated, a main menu is presented in the form of a list of those of the switching devices and the telephones which can be controlled from that input station. By use of the input switching device and the menu display, a switching device or the telephone can be selected for control. If control involves more than switching power on or off to an appliance, a new menu appears listing the various functions to be chosen, e.g. television channel, volume control. Each controlled switching device has one or more relays having controlled switch contacts to be connected in the power supply lines to the controlled appliance and, if necessary, to means for adjusting some function of the controlled appliance, such as television channel, sound volume, and so forth.

Switching relays were, and are, used in switching devices controlled by the control units of PSU1 and PSU3 systems for the same purpose. Each such switching device has a three pin mains input plug to be inserted into a domestic or hospital mains output socket, and has a mains power output socket into which the mains plug of the controlled appliance is inserted. It has been found that, in a domestic environment, when the disabled user is no longer in a particular room containing say a television, an electric fire and a table lamp, all of which are connected to a control system used by the disabled person when in that room, an able-bodied attendant wishing to use these appliances will unplug them from the control system and plug them directly into the domestic mains output sockets. A result of this action is sometimes that the able-bodied attendant forgets to unplug the appliances from the domestic mains output sockets, re-plug them into the switching devices, and plug the switching devices into the domestic mains output sockets before the disabled user returns to the room. Although such an occurrence can easily be dealt with if the attendant is still present when the user wishes to control the uncoupled appliances, there may be no attendant present when the user wishes to have control, so that there may be inadequate heat or light, or no entertainment in the room. Preferably therefore, an embodiment of the present invention includes means which allow an able-bodied attendant to share with a disabled user control of at least one control function of the system without the able-bodied attendant having to utilize an input adapted for use by a disabled person, or to disconnect a controlled appliance from the system. Preferably such means is in the form of a manually operable push button switch incorporated in a controlled switching device of the system, the state of this push button switch being sensed by a control unit of the system and the control unit changing the state of the switching device in response to each actuation of the push button switch, so that when an appliance is coupled to that switching device, the state of the appliance is changed at each actuation of the push button switch. The control system preferably, of course, indicates such changes of state so that when a disabled user reassumes command of the system, or that portion of the system which includes the push button switch, the current state of the appliance is immediately apparent to him or her, and can be changed, if desired, to the other state through the operation of an input adapted for use by the disabled user.

The invention will now be described in more detail, solely by way of example, with reference to the accompanying drawings, in which:

FIGS. 2 to 9 are illustrations of displays which may be presented by the apparatus of FIG. 1;

Figure 1:
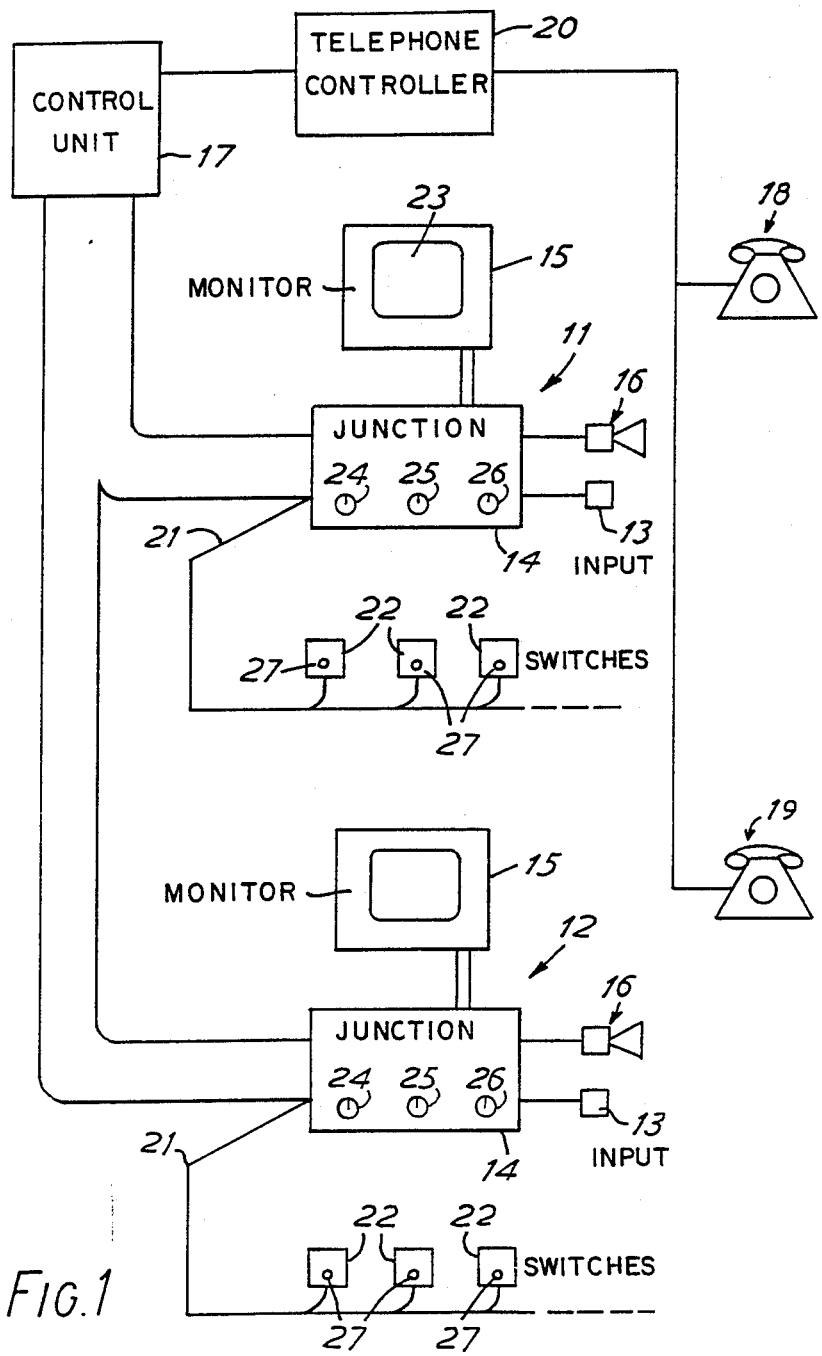
FIG. 1 is a block diagram of microprocessor-based environmental control and communicator apparatus embodying the invention.

FIG. 1 is a block diagram of a control apparatus embodying the invention and having two input stations 11 and 12. Each input station has an input switching device 13 operable by a severely physically disabled person, a switching and junction unit 14 which houses a battery (not shown) and power supply and battery charging circuitry (not shown), a television-type monitor unit 15, and a master intercom unit 16. The input stations 11 and 12 are situated in different rooms and are both coupled to a control unit 17 which includes a microprocessor (not shown) and associated processing and storage circuitry (not shown).

The control unit 17 is also coupled, through an LST9 controller 20, which is a telephone control apparatus approved by British Telecom, to two loudspeaking telephone sets 18 and 19 sited respectively in the rooms in which the input stations 11 and 12 are located.

A serial bus 21 connects the control unit 17 to controlled switching devices 22 in the rooms containing the stations 11 and 12 through the respective switching and junction units 14. The switching devices 22 may control simple on/off appliances such as electric fires and lamps, and groups of functions of more complex appliances such as television sets, radio sets, and controlled beds. Each switching device 22 is provided with encoding switches which give it an identifiable address code so that the control unit 17, by poling the devices 22 in sequence, can determine which devices are present. The switching and function units 14 are also provided with coding means which enable the control unit 17 to determine which input station is being used.

The coding means of a switching and junction unit 14 includes encoding switches which give it an identifiable address code, and means for indicating by a status signal the status of the input switching device 13 connected to the unit 14, i.e. whether or not the device 13 is being actuated. The status signal may be simply a single bit which is 0 whenever the switching device 13 is not actuated and 1 whenever the device 13 is actuated.

The address code of each switching device 22 includes two bits which associate the particular device 22 with the input station 11 and 12 sited in the same room as that device 22. Thus the control unit 17 is able to address commands specifically to only those devices 22 which are in the room containing the input station 11 or 12 which is in use, since the command signals can include the room identity in the form of the two bits of the address code of the device 22 which is to be controlled, and the devices 22 can be provided with a comparison circuit or gating circuit which ensures that only the intended device 22 responds to the command signal.

The control unit 17 is also adapted to actuate only the monitor unit 15 of whichever input station 11 or 12 it detects as having an actuated input switching device 13 first after a predetermined length of time in which no input station has presented an actuated input switching device 13. This prevents more than one input station being used at the same time, and reduces the risk of accidental disabling of the input station currently in use. The monitor unit 15 of the last used input station remains activated unless a changeover to another input station occurs through the use of the input switching device 13 of that other input station after the predetermined length of time.

The single LST unit 20 shown is actuated whichever input station 11 or 12 is used to control the telephone system. However, the speaker/microphone units 18 and 19 are switched into or out of operation as required. Under present British Telecom regulations this switching must be done manually by a helper. However, it is possible as a practical matter to effect the switching under the control of the active input station and the control unit 17 if respective switching devices 22 of the serial link 21 are used to control coupling of the speaker/microphone units 18 and 19 to the LST unit 20. Alternatively, to comply with present British Telecom regulations, more than one LST unit, one for each speaker/microphone unit in the system, may be used and controlled directly from the control unit 17.

When the control unit 17 senses that one of the input stations is in use, for example, station 11, as a result of operation of the input switching device 13, the monitor unit 15 of that station is energised and caused to present initially a main menu on its screen 23. An example of a main menu is illustrated in FIG. 2. This main menu has two wide columns of eight rectangular row areas. A blank area remains on the screen below this menu to provide space for a variety of messages which may be displayed from different sources. By colour, the top row area of the left hand column is indicated as being active. For example, the active state may be an orange background, the other row area of both columns having a green background. By operating the input switching device 13, the user can cause the active background colour to scan down the row areas of the left hand column and then up the row areas of the right hand column. To select for operation the device or function indicated in any row area of a column, the input switching device 13 is operated while the particular row area of a column is showing the active background colour. The row area of a single column will now be referred to as a cell. For example, to cause an audible and visible alarm to be activated, the user initiates the scanning operation and selects the cell with the word ALARM displayed. If the telephone rings, the SEIZE LINE cell is selected by the user if he wishes to receive the call. The foreground colour, i.e. colour of the lettering, in the active cell may also differ from the foreground colour in other cells and be controlled in the same way as the active background colour.

A detailed description of the manner in which the operation of an input switching device such as the device 13 is related to selection of a displayed function or device and control of the selected function or device is given in patent specification GB No. 2 137 001 which is incorporated herein and to which reference should be made for such information.

When a device or set of devices or functions is selected on the main menu and requires, for proper operation, further choices by the user, selection of the appropriate cell of the main menu results in replacement of the main menu by a special menu relating to the selected cell. For example, selection of the INTERCOM cell of the main menu results in replacement of the main menu by the intercom menu illustrated in FIG. 3.

On first appearance, the top left hand cell of the intercom is active. Scanning is carried out as for the main menu. If RESET is selected, the main menu reappears. DOOR 1 and DOOR 2 are electrically controlled door locks. INTERCOMs 1 to 4 are sited where required, for example outside the front door, which may be DOOR 1, in the kitchen, and two other rooms. CALLS 1 to 4 are audio signal generators sited at suitable places to enable the user to signal for assistance easily.

FIGS. 4, 5, 8 and 9 illustrate the special menus called up by selection of, respectively, SOCKETS #1, TELEPHONE, TELEVISION and COMMUNICATIONS on the main menu (FIG. 2).

SOCKETS #1 allows selection of a fan, a heater, a lamp, an electric blanket, and three further electrically controllable devices powered respectively through controlled sockets 05, 06 and 07.

TELEPHONE allows control of dialing out from the telephone set in the room with the active input station, and storage of telephone numbers for future use. Selection of TELEPHONE causes FIG. 5 to be displayed. To call a stored number, for example the social services number, SEIZE LINE is selected, then SOCIAL SERVICES, then DIAL OUT. To increase the volume of the incoming speech HIGH VOLUME can be selected. To end a call, SEIZE LINE is selected. To call a number not stored, the temporary store cell TS is selected, then SET UP NUMBER is selected, which causes the menu of FIG. 6 to replace that of FIG. 5. The digits of the number can then be selected. The HYPHEN is used to insert a suitable delay between area code and local exchange, for example. Mistakes can be corrected one digit at a time by DELETE. The space on screen below the menu is used to display the telephone number digits selected. If construction of a number is interrupted and the display reset to the main menu, editing of the number can be resumed on recalling the menu of FIG. 6 by then selecting RESUME EDITING, the partly constructed number being recalled on return to the menu of FIG. 6. When the correct number is complete, ENTER NUMBER is selected, and the menu of FIG. 6 is replaced by that of FIG. 5. The entered number is located in a temporary store identifiable at TS in FIG. 5. SEIZE LINE is selected, then TS and finally DIAL OUT. To enter or change a number in a "permanent" store location, i.e. one of those identifiable at A1 to A7 in FIG. 5, the required cell must be selected in the FIG. 5 menu before the SET UP NUMBER cell is selected. For example, if the social services telephone number changes, the A7 cell is selected, then SET UP NUMBER. The new number will then be entered into the A7 "permanent" store when ENTER NUMBER is selected in the FIG. 6 menu. To give the stored numbers names or identifying codes on the FIG. 5 menu, SET UP NAME is selected after selecting the required one of cells A1 to A7. The menu of FIG. 7 then replaces that of FIG. 5 and the name or code can be composed from the symbols displayed there, the selected symbols appearing in the space on screen below the menu. The letter combinations RST, SPC, D/C, D/L, R/E and ENT are control codes which upon selection cause, respectively, the following operations to be executed:

RST: Reset to main menu
SPC: Space
D/C: Delete character
D/L: Delete line
R/E: Resume editing
ENT: Enter name To allow a large number of telephone numbers to be stored, several further menus may be accessible which are each substantially identical to the FIG. 5 menu except that the right hand column is entirely of "permanently" stored number cells, and the NEXT PAGE cell in the left hand column indicates the cells of the next menu's right hand column. For example, selection of NEXT PAGE in the FIG. 5 menu causes a new menu to appear in which the right hand column has cells B1 to B8. If there is a further such menu available, the NEXT PAGE of this new menu will indicate (C1–C8) as the right hand column of the further such menu. The last of these additional menus will indicate at NEXT PAGE that that cell on selection will return the user to FIG. 5, the display in cell 6 being

NEXT PAGE (TS-A7)

Selection of TELEVISION on the main menu replaces that menu with FIG. 8 which allows the various functions of the particular television set in the room containing the active input station to be selected.

The first selection of COMMUNICATIONS on the main menu after switching on of the system replaces FIG. 2 with FIG. 9 which allows the user to compose messages on the screen space below the FIG. 9 menu. Up to four lines of text can be composed in this space. Further composition results in automatic scrolling so that the top line of the four is lost. Lines lost in this way are not stored unless a storage function, described below, has previously been selected. Subsequent selection of COMMUNICATIONS on the main menu recalls whichever COMMUNICATIONS menu was last on screen.

Commands included in FIG. 9 are:
RST: Reset
SPC: Space
D/C: Delete character
D/L: Delete line
CR: Carriage return
/c: lower case
RPT: Repeat
CMD: Command Selection of 1/c causes the menu of FIG. 9 to be replaced by a similar menu in which all the alphabetic symbols are in lower case, and the command 1/c is replaced by U/C which is the command for Upper Case and replaces the lower case menu with FIG. 9.

The CMD command is used to call up a new menu which displays a choice of communication functions relating to a printer, a computer and videotext. One of the functions selectable on the new menu is a store function which hen selected causes symbols subsequently selected from either 1/c or U/c menus to be stored. Selection of the printer function will then cause the stored text to be printed out.

For ease of select[on, in the COMMUNICATION menus and the menu of FIG. 7, the whole row which includes the currently active scanning cell may be underlined or contrasted so that the user can see when his target lines up with the currently active scanning cell.

The space on screen below the currently displayed menu displays messages from three other sources in addition to the COMMUNICATION menus.

These are:
1. Status information, i.e. what appliances are in operation, e.g. electric fire, electric blanket, television, tape recorder, electrically-controlled curtains, etc.
2. System prompts, e.g. which intercom is operating, which telephone repertory store is being dialed out and a connection made.
3. Error diagnostic messages from the system for assisting service engineers if the system develops a fault.

When the space below menu is being used for communications to be printed by the printer, a correspondence window receiving 4 lines by 40 characters is defined so that a display corresponding to two lines of 80 characters for A4 format can be shown.

Figure 10:
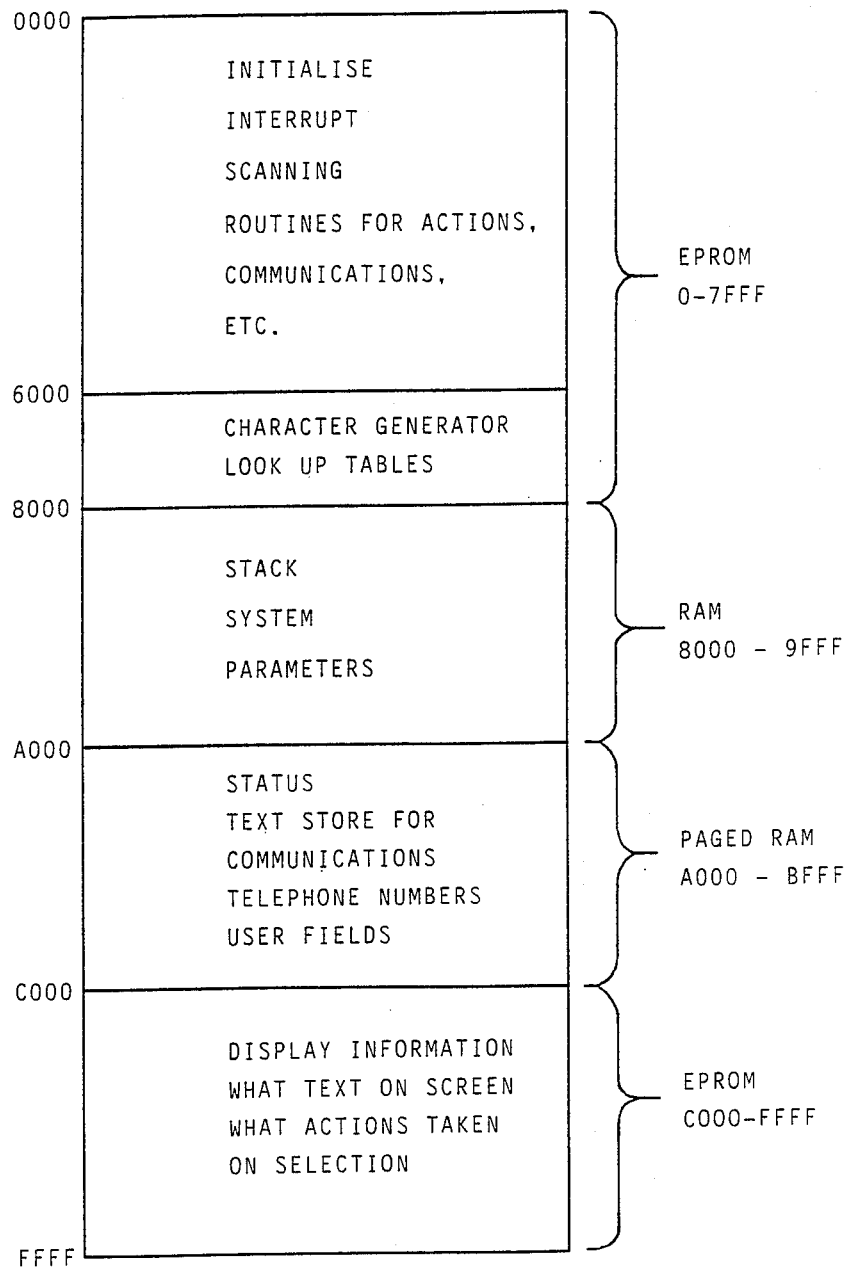
FIG. 10 is a memory map of the apparatus of FIG. 1.

The apparatus of FIG. 1 uses a single microprocessor as its central processing unit. This microprocessor is, in a constructed example of the apparatus, a Zilog Z-80 microprocessor, and has an 8-bit data bus and a 16-bit address bus connected to it. FIG. 10 is a memory map showing the principal divisions of the 64K memory space addressable by the address bus. The sizes of the five areas into which the map is divided are indicated in hexadecimal notation at the left-hand side of the map. The types of memory devices used for the different areas is indicated at the right-hand side of the map. From 0000 to 6000 bytes is read-only memory occupied by initialisation, interrupt, scanning, routines for actions, communication and other programs. From 6000 to 8000 bytes is read-only memory occupied by character generator programs and look-up tables for determining the appearance of screen displays. From 8000 to A000 bytes is read/write memory used as stack storage and for storing data relating to the configuration of the system.

Figure 11:
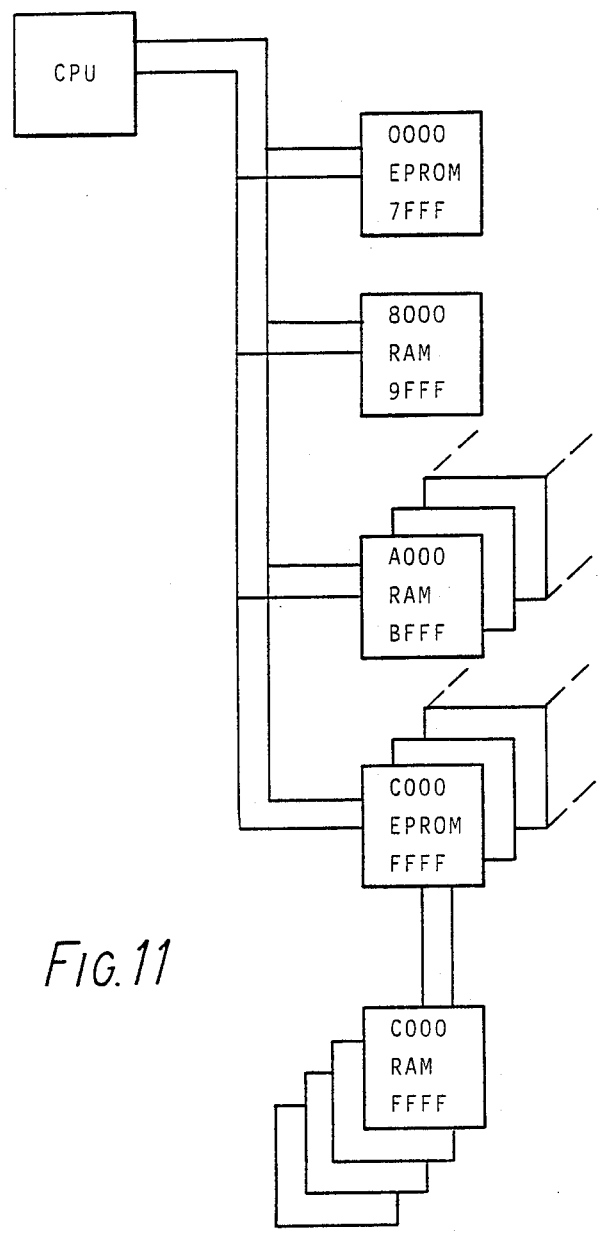
FIG. 11 is a block diagram illustrating microprocessor and memory devices of the apparatus of FIG. 1.

From A000 to BFFF bytes is also read/write memory and is used to store the current status of the system, text being generated and edited for communication and printing, telephone numbers and associated information, and other user fields. From C000 to FFFF bytes is read-only memory occupied by data determining the various fixed aspects of the displays, and the action codes associated with selection of menu cells. The addresses C000 to FFFF are also used for another, paged area of read/write memory, not shown in FIG. 10, which is used in determining the displays presented by the screen of an active input station. FIG. 11 shows schematically the CPU coupled to the various EPROM and RAM devices used to make up the memory areas. The RAM area A000 to BFFF is paged so that there are 8 pages of 8K bytes each. Similarly, the EPROM area C000 to FFFF is paged so that there are 8 pages of 16K bytes each. The pages of these two RAM and EPROM areas are given the same page numbers and the I register of the Z-80 microprocessor is used to store the page number.

The RAM area at C000 and FFFF is also paged, having 16 pages of 16K bytes.

When power is switched on, the apparatus of FIG. 1 carries out the initialisation program first of all. The principal steps in the initialisation program are:
1. Set up all system parameters to starting condition.
2. Reset all status information.
3. Reset all serial bus outputs.
4. Set up active input station, read scan rate, input mode, scanning delay, and other input station status data.
5. Set up system registers.
6. Clear active display screen.
7. Scan serial bus to detect all devices present, and set up table storing this data.
8. Set up main menu on active screen.
9. Jump to scan program.

At the beginning of the scan program, a loop is run in which the output of the input switching device 13 is monitored for a change indicating the beginning of a scan. Initialisation, scanning, selection and control programs which can be adapted for use in the present apparatus are described in GB No. 2 137 001B.

Each of the input station junction and switching units 14 has manually settable switches such as 24, 25 and 26 for setting a scan rate, input mode, and scanning delay, as in the apparatus of GB No. 2 137 001B or in the apparatus of GB No. 2 058 419. The states of these switches are sensed by the CPU in step 4 of the initialisation program. The scan rate, input mode and scanning delay of each one of the input stations 11 and 12 are independently settable, so that the input stations can be adapted for use by different users respectively, e.g. two patients in a ward. The various manually operable switches must be set in the appropriate states by a helper.

The switching devices 22 coupled to the serial bus 21 control appliances such as electric fires, radio, television, door locks, curtains, bed adjusting mechanisms, and tape recorder, and any other electrically powered appliances whose functions can be controlled by relays or relays and control motors. Each device 22 has a UART which receives serial data from the CPU in the control unit 17 and transmits serial data back to the CPU. The output of the UART to the device 22 is coupled through a decoder to the one or more control relays of the device. The input of the UART from the device 22 is coupled from manually settable encoding switches which identify the particular device and indicate what relay switches are controlled by the device 22. The current states of the controlled relays can be sensed from internal status registers of the UART and such data is read by the CPU as required. The identity code of the device 22 established by the manually settable switches is also used by the UART to ensure that the device responds only to commands intended for that device. At step 3 of the initialisation program, the CPU ensures that all devices which may be present are in a safe condition, which is the reset condition. In this particular example, a total of 126 devices can be controlled. Each device 22 has a seven bit identification code.

Each device 22 also has a manually operable push button switch 27 the state of which is also sensed by the control unit 17 through data transmitted by the serial link 21. Whenever the push button 27 is operated, the control unit 17 changes the state of the associated appliance, i.e. from ON to OFF, or from OFF to ON. The change of state is indicated on the screen of the active monitor 15.

The interrupt program is a program run every 20 milliseconds and consists in the transmission of one device address and the currently required command for that device, this transmission occupying 7 milliseconds and being effected at 2400 baud over the serial bus 21. The control unit 17 has a UART for this purpose which also receives any response from a device 22 which is present and has the currently transmitted address. The state of the device 22 is encoded at the device and transmitted back to the control unit 17 together with the identification code of that device. At the control unit 17, the CPU receives automatic confirmation of each transmission by its UART, feedback being provided. Identification and status data is only received by the CPU if the currently addressed device 22 is present. Status data from a device 22 is preferably transmitted as a 16 bit parameter and compaction is used to ensure economical use of data bits, i.e. no bits are assigned to status conditions which are effectively constant. When no commands are being input by the user, the interrupt program runs on a preset sequence through the addressing of the possible 126 devices 22. However, whenever a selection is made by the user that involves an operation at a device 22, the interrupt program sequence of addressing of the devices 22 is altered so that the sequence starts with the device which is to be controlled.

In the scanning program, as a cell is made active, a code corresponding to that cell is read and, if the cell is selected by the user, the action corresponding to the read code is executed. The action may be to set up a new menu or to turn a status on or off and execute a control function accordingly. A new menu may be set up directly from EPROM, or indirectly by means of a table held in RAM. The code corresponding to each cell includes an action code, which is translated into an address for a routine for carrying out the required setting up of a new menu, or changing of status and execution of the associated control function.

The display seen by the user measures 48 characters wide and 16 lines deep, the menu occupying the top 12 lines and the message space below the menu occupying 4 lines. The memory area allocated to a screen display corresponds to 16 lines of 64 characters, with each character being 16 pixels wide and 16 pixels high. Each pixel corresponds to one memory bit so that the total memory space required is $16 \times 64 \times 16 \times 16$ bits, or 32 kilobytes. These 32 kilobytes are organised as two pages of 16 kilobytes at C000 to FFFF in RAM. To provide colour information, a further 32 kilobytes are allocated, again organised as two pages of 16 kilobytes at C000 to FFFF in RAM. One page of colour information is used to determine the colours of the character forms, and the other page to determine the colours of the character backgrounds. The value, 0 or 1, of each pixel determines whether the colour selected is the form, or "ink", colour, or the background, or "paper", colour.

Each line of 16 pixels of each character has associated with that line 16 bits of colour data of which 8 bits determines the ink colour and the other 8 bits determines the paper colour. Which of the ink colour and the paper colour appears at any particular pixel depends on the value of that pixel bit. Characters may be composed of horizontal lines of pixels which have different ink colours and different paper colours so that vertically distributed multicolour effects can be obtained.

Permanently stored data for determining the appearance of the various displays is held at the EPROM areas 6000 to 8000 and C000 to FFFF, as indicated in FIG. 10. Character generator data determines, in conventional manner, the pixel structure of different characters. Data relating to graphic and colour aspects of individual displays and the characters to appear are stored in compact coded from since pixel maps of such aspects are not required in permanent form. Thus the amount of memory area required to store the permanent features of the displays is relatively small.

Figure 12:
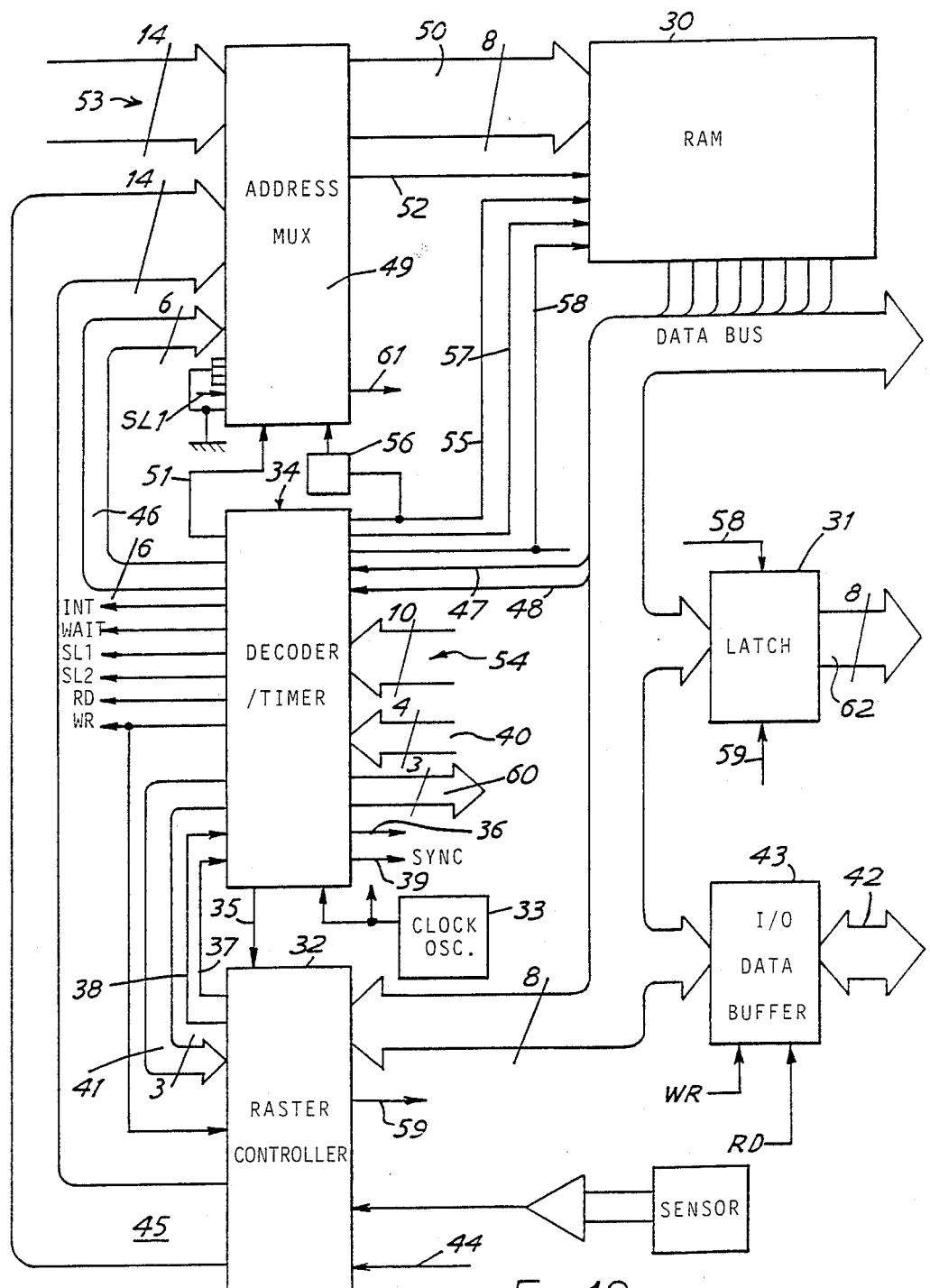
FIG. 12 is a block circuit diagram of part of the circuitry of the apparatus of FIG. 1 associated with display control.

FIG. 12 shows in detail the circuitry controlling the RAM at C000 to FFFF, which is there represented by a block 30. The RAM 30 is formed by eight dynamic ram integrated circuits, each of which is addressed in nibble mode and has four distinct regions of 64 kilobits each. A suitable device for each of the eight integrated circuits is a 41257P-15 such as the Toshiba TMM 41257P15. Each nibble mode dynamic ram circuit has a single input/output data terminal. The eight data terminals of the RAM 40 are connected to respective conductors of the 8-bit data bus.

Within each nibble mode ram circuit, the four distinct 64 kilobit regions are allocated respectively to ink bits, paper bits, first pixel bit and second pixel bit. Each 64 kilobit region has a single input/output data terminal, and the four data terminals are coupled through an internal multiplexer to the single data terminal of the respective nibble mode ram circuit. In a read operation, respective single bits are read out in fixed sequence, determined by an internal counter, from the four 64 kilobit regions so that four bits, which are ink, paper, pixel and pixel bits respectively, appear in sequence at the data terminal of the nibble mode ram circuit. The result for the complete RAM 30 is that four bytes of data are supplied in sequence to the data bus, the first byte being ink, the second paper, and the third and fourth both representing eight pixels. Thus the sequence of four bytes provides the ink colour data, paper colour data, and the 16 pixels for a single line of pixels of a single character. These four bytes are latched, one after the other, by a video data latch 31 connected to the data bus.

To ensure that the video is data read out in the correct sequence, a programmable video raster controller, which operates as an address controller and sync generator 32 is provided. A 16 megahertz oscillator 33 acts as a clock oscillator for the video circuitry and supplies 16 megahertz clock pulses to a decoder/timer circuit 34, formed by four programmed logic array circuits, such as four SN74PL/6R8-1 circuits, programmed to generate 1 megahertz and 2 megahertz outputs 35 and 36. The 1 megahertz output is supplied to the raster controller 32 which, in response, generates vertical and horizontal raster sync signals 37 and 38 which are supplied to the decoder/timer 34, which produces a composite sync signal 39. In the initialisation program, the CPU accesses the raster controller 32 by means of control signals applied on a control bus 40 to the decoder/timer 34 and decoded there to produce a write command WR and three further bits of command on a bus 41 to the raster controller 32. Data for the programming of the raster controller 32 is entered from the main data bus 42 through the input portion of an input/output data buffer 43 coupling the main data bus 42 to the video data bus, which is connected to the raster controller 32 as shown in FIG. 12. To clear the raster controller 32 initially, a system reset signal is applied to an input terminal 44 of the controller 32.

During a display, the controller 32 is driven by the 1 megahertz output 35 from the decoder/timer 34 and produces a sequence of addresses on a 14 bit bus 45. The remaining 2 bits of the address are applied on two lines of a 6 bit bus 46 from the decoder/timer 34 and are latched versions of the bits 6 and 7, i.e. the last two bits, on the video data bus, the lines for these two data bits being connected as shown to the decoder/timer 34 at 47 and 48 respectively. The pair of bits selected to be latched are two ink byte bits, these bits being spare since all the required colours of ink are encoded by six bits, and the two latched bits give one of four possible addresses. These four correspond to the division of each of the 6 kilobit regions of each nibble mode ram into four 16 kilobit subdivisions, each such subdivision containing the respective data relating to one complete screen display. Thus the first 16 kilobit subdivision of the first 64 kilobit region of the first nibble mode ram contains all the first bits of the ink data of one screen display, the first 16 kilobit subdivision of the second 64 kilobit region of the first nibble mode ram contains all the first bits of the paper data of the same screen display, and respective first 16 kilobit divisions of the third and fourth 64 kilobit regions of the first nibble mode ram contain all the respective first bits of the two pixel bytes of that same screen display. The other seven bits of all the ink, paper and pixel bytes for said one screen display are stored in the first 16 kilobit subdivisions of the 64 kilobit regions of the remaining seven nibble mode rams. A multiplexer 49 applies the sixteen address bits to the RAM 30 in two bytes over a bus 50. The multiplexer 49 may be formed of five 8-to-2 multiplexer circuits such as the 74ALS153 type. The second 16 kilobit subdivision of each 64 kilobit region contains bits for another screen display. Similarly the third and fourth subdivision of each 64 kilobit region may contain, respectively, bits for another two screen displays. It is consequently possible to switch from one stored pixel map to another at any chosen character in a display. Thus windowing, i.e. changing from one display to another over a selected part of a screen only, is possible. Also, the switchover from a current pixel map stored in, for example, the set of 32 first 16 kilobit subdivisions, to a new pixel map stored in, for example, the set of 32 second 16 kilobit subdivisions, can be implemented substantially instantaneously in response to simply changing two bits in the first ink byte of the current pixel map, this change being effected by writing in the changed bits from the main data bus 42 under the control of the CPU. Thus the RAM 30 can be used as a double buffered RAM in which the writing in of the next display is completed during the reading out of the current display, and the changeover effected by a simple switching from the current display store to the next display store.

The multiplexer 49 selects addresses from the raster controller 32, with two bits from the decoder/timer 34, in response to one state of a control signal 51 from the decoder/timer 34. The addresses are applied by the multiplexer 49 in two groups of nine bits, the ninth bit of each group being applied over a line 52 which determines the sequence of operation of the internal counter of each of the eight nibble node ram circuits. The internal counter has four states, each one causing the internal multiplexer of the ram circuit to select a respective one of the four 64 kilobit region data terminals for connection to the data terminal of the respective ram circuit. The two inputs to the multiplexer 49 corresponding to the output supplied over the line 52 are both grounded in the case of the multiplexer inputs selected by the state of the control signal 51 which is presented for reading out the pixel map for the current display. Two lines of the bus 46 from the decoder/timer 34 to the multiplexer 49 convey two input bits which correspond to the output on the line 52 when the control signal 51 sets the multiplexer 49 to select address bits presented on 14 lines 53 of the main address bus from the CPU. The two bits from the bus 46 determine one of four possible outputs for the line 52, which one being determined by the signals on the two least significant address bits on the main address bus, ten lines of which are applied at 54 to the decoder/timer 34. It is thus possible to write into the four 16 kilobit subdivisions of the 64 kilobit regions of the nibble mode ram circuits selectively from the main data bus 42. The remaining two lines of the bus 46 are driven from the next two least significant bit lines of the main address bus 53, these two lines also being included in the set of ten lines 54.

The selection of which set of nine inputs is applied to the output terminals of the multiplexer 49 is determined by the state of a further control signal 55 applied through a 15 nanosecond delay 56 from the decoder/timer 34. This signal 55 is also applied to the RAM 30 for latching. Two more control signals 57 and 58 developed by the decoder/timer 34 are applied to the RAM 30. The signal 58 is a reset signal for the internal counters of the nibble mode ram circuits, and the signal 57 is a read/write signal. The reset signal 58 is also supplied to the load terminals of the video data latch 31. A blanking signal 59 that clears the latch 31 is supplied by the raster controller 32 to blank out video signals during the horizontal and vertical raster flyback times.

The decoder/timer 34 develops six control signals, comprising RD, SL1, SL2 and three bits on a bus 60. The signal RD is applied to hold the input/output data buffer 43 in its output state so that the CPU can read the contents of the RAM 30 for test purposes. The other five control signals SL1, SL2 and the three bits on bus 60 are applied to circuits shown in FIG. 13. The decoder/timer 34 also develops a WAIT signal and an interupt signal INT for the CPU, to control writing accesses to the RAM 30 and synchronisation of CPU operations with the vertical sync signal, which is used to generate the INT signal, the processing frames of the CPU thus being synchronised with the video raster field sync signals. The various control signals developed by the decoder/timer 34 are determined by address bits and control signals from the CPU address bus 53 and the CPU control bus 40.

Part of the decoder/timer 34 is programmed and arranged to operate as a state machine driven by the clock oscillator 33 to generate 1 megahertz, 4 megahertz and 8 megahertz signals.

The control signal SL1 is also applied to one input terminal of the multiplexer 49 and determines the state of a control signal 61 produced by the multiplexer 49 during the first byte of a read operation of the RAM 30, the signal 61 being grounded through the multiplexer 49 at all other times.

Figure 13:
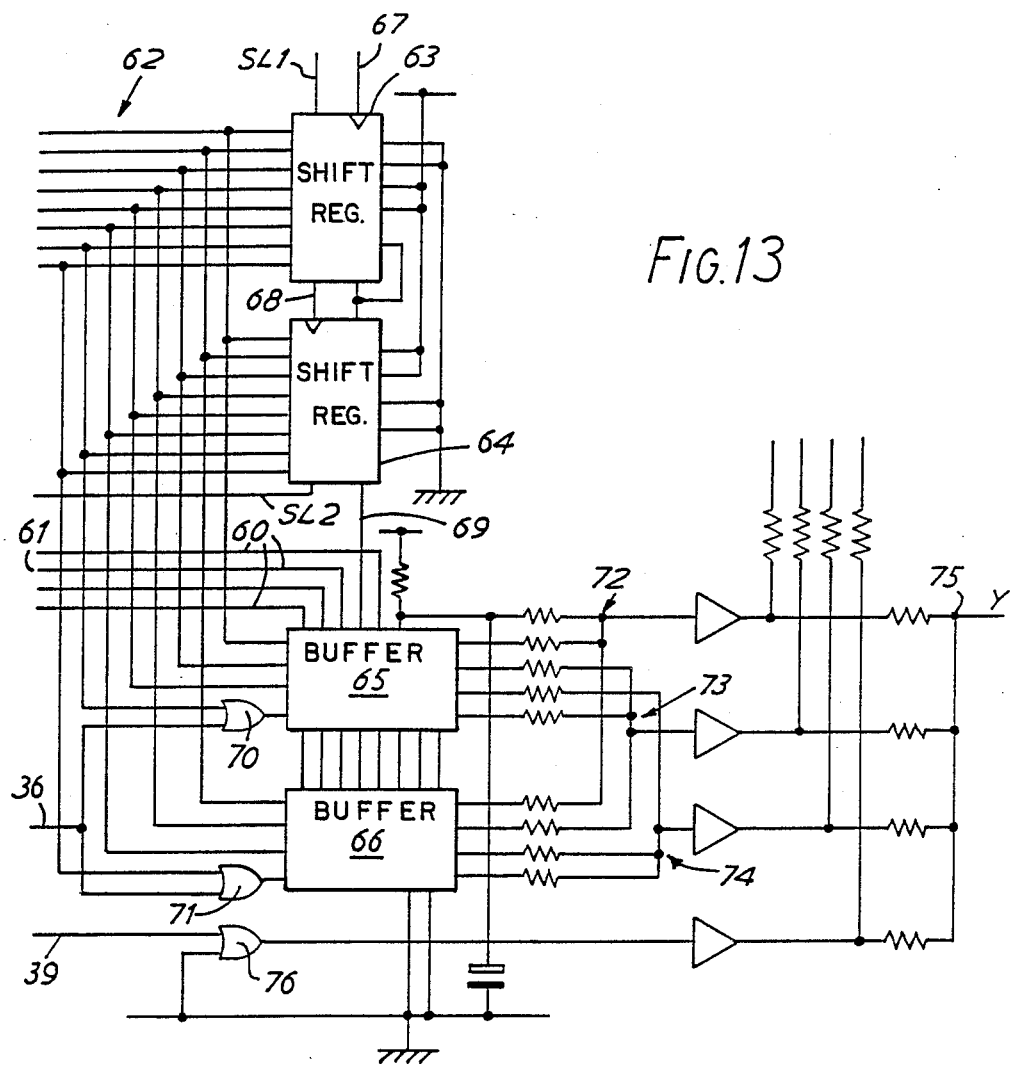
FIG. 13 is a detailed circuit diagram of another part of the circuitry of the apparatus of FIG. 1 associated with display control.

Data latched by the latch 31 is presented on an 8-bit video data latch output bus 62 which, is shown in FIG. 13, is connected to the parallel input terminals of two cascaded 8-bit shift registers 63 and 64, and a pair of 4-bit simultaneous read/write buffers 65 and 66. The shift registers 63 and 64 are supplied the 16 megahertz clock signal from the clock oscillator 33 at clock input terminals 67 and 68. The control signals SL1 and SL2 are supplied to the shift registers 63 and 64 respectively as shown and serve as load commands for loading the 8-bit parallel input from the bus 62. The timing of the load commands SL1 and SL2 is such that, during each reading out from the RAM 30 of an ink byte, a paper byte and two pixel bytes, the shift register 63 is loaded with the first pixel byte from the RAM 30 and the second pixel byte from the RAM 30 is loaded into the shift register 64. Whenever the shift register 63 is loaded, the previous 8-bits of data from the previous character have already been shifted into the shift register 64. The shift register 64 is loaded after the sixteen bits forming the two pixel bytes of the previous read out have been all shifted out as serial output at its serial output terminal 69. The two pixel bytes read out at each nibble from the RAM 30 occur 125 nanoseconds apart, which is equivalent to the duration of the two serial bits. This unwanted interval is eliminated by delaying the output of the shift register 63 by 125 nanoseconds so that when the second byte of pixel data is loaded into register 64, the sixteen bits of the two bytes are in the required order and there is no gap. Thus the first byte from the RAM 30 becomes the second byte in the serial output from the register 64.

In the circuit of FIG. 13, the two shift registers 63 and 64 are each 74LS 166A circuits, each having these pins 6,8,9 and 16 grounded, and pins 1 and 13 of the register 63 connected together as shown and to pin 1 of the register 64.

Each of the simultaneous read/write buffers 65 and 66 has four 4-bit registers with three-state parallel outputs. The four inputs to each register are connected to four data input terminals of the respective buffer, those of the buffer 65 being connected to three lines of the bus 62, and the output of an OR-gate 70, and those of the buffer 66 being connected to three other lines of the bus 62, and the output of an OR-gate 71. The OR-gates 70 and 71 each have two inputs which are respectively connected to one line of the bus 62 and to the 2 megahertz output 36 from the decoder/timer 34. The buffers 65 and 66 also each have three control input terminals connected to the three lines of the bus 60 from the decoder/timer 34 and one control input terminal connected to the output 61 of the multiplexer 49.

The control signals on two of the lines of the bus 60 determine which pair of registers in each buffer 65 or 66 can be written to and which pair can be read from. The signal on the line 61 determines which one of the pair written to is loaded by the current data input, and the pixel output signal on terminal 69 determines which one of the pair read from is coupled to the four output terminals of the respective buffer. The third line of the bus 60 supplies a write pulse to the buffers 65 and 66.

Whenever an ink byte appears on the bus 62, the two most significant bits are masked at the OR gates 70 and 71 by the 2 megahertz signal on line 36, and the eight bits presented to the buffers 65 and 66 are loaded into two 4-bit registers, one in each buffer. Whenever a paper byte appears on the bus 62, all eight bits are loaded into two other 4-bit registers, one in each buffer. The ink and paper data held in the other four registers are read out to the total of eight data output terminals of the two buffers 65 and 66, ink or paper being selected in dependence upon the state of the pixel signal on terminal 69. By the timing of two of the bits on bus 60, it is arranged that the registers containing ink and paper for a set of sixteen pixel bits become the currently read out set just at the time that the first of these sixteen pixel bits is output from the register 64.

The eight data output terminals of the buffers 65 and 66 are connected to four digital to analog converters 72, 73, 74 and 75 formed by summing resistors as shown in FIG. 13 and provide analog blue, red, green and luminance signals respectively for the active monitor 15.

The composite sync signal 39 developed by the decoder/timer 34 is supplied through an OR gate 76 to the monitor 15 directly and combined in the converter 75 to produce a complete luminance signal Y.

In the circuit of FIG. 13, the buffers 65 and 66 are 74ACT670 circuits.

Figure 14:
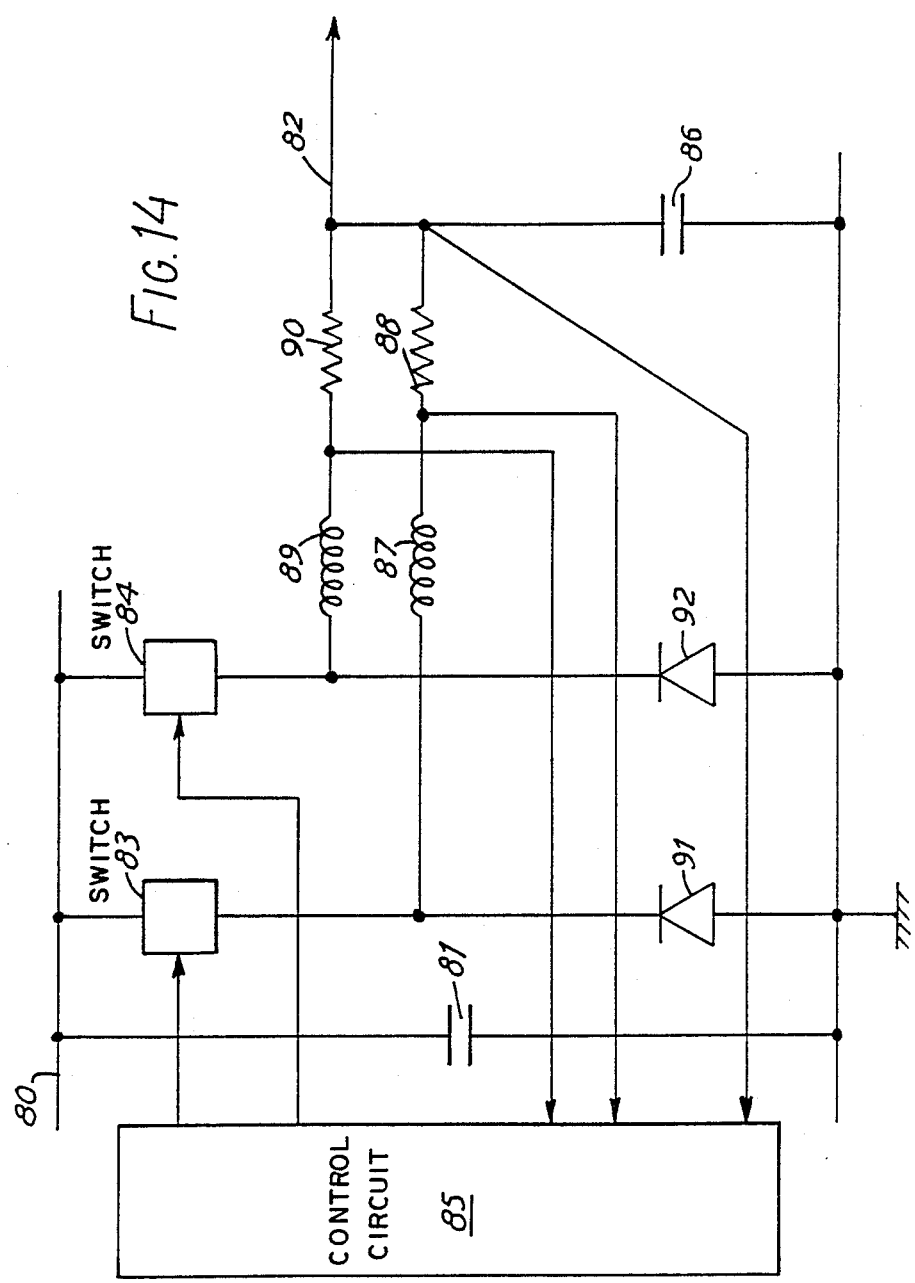
FIG. 14 is a circuit diagram of a power supply of the apparatus of FIG. 1.

FIG. 14 shows the circuit used as a battery charging circuit in each junction and switching unit 14. The same form of circuit is also used in the control unit 17 as a low voltage supply circuit supplying 5 volts, d.c. The battery charging circuits supply 13.8 volts, d.c. at their output terminals.

The circuit of FIG. 14 is supplied from a 30 volt d.c. rail 80 coupled to ground by an input capacitor 81. Direct current is allowed to pass to the output terminal 82 by two switches 83 and 84 which are rendered conducting at different times by a control circuit 85. The output terminal 82 is coupled to ground by an output capacitor 86. A series combination of an inductor 87 and a resistor 88 couple one terminal of the switch 83 to the output terminal 82, and another such combination 89,90 couple one terminal of the other switch 84 to the terminal 82.

Flywheel diodes 91 and 92 allow load current to circulate without passing through the source connected to the supply rail 80 or the switches 83 and 84.

Current feedback for control purposes is obtained by feedback of the voltages across the resistors 88 and 90 to the control circuit 85.

The control circuit 85 causes the switches 83 and 84 to operate with a mark/space ratio of approximately 1:1, and to be 180° out of phase, i.e. so that the switch 83 is conducting when the switch 84 is non-conducting, and the switch 83 is non-conducting when the switch 84 is conducting. As a result, the maximum current passed by each switch 83,84 is only half the magnitude that would be passed by a single switch providing the same output current at the terminal 82. Similarly, the components 87 to 92 are subjected to approximately half the maximum current that would exist in a single component circuit. Also, the input and output ripple amplitudes are small, being a minimum with the mark/space ratio 1:1.

A circuit with three switches, three flywheel diodes, and three inductor-resistor combinations can be constructed and can be operated to minimise the maximum currents and input and output ripple amplitudes.

The reduced input ripple allows a lower capacitance than conventional for a corresponding single switch circuit to be used as the input capacitor 81. The switches 83 and 84 produce respective out of phase ripple currents in the resistors 88 and 90. These ripple currents are equal in amplitude and opposite in phase and when summed tend to cancel out leaving a very low residual ripple at the output terminal 82. The frequency of the residual ripple at the output terminal 82 is mathematically the product of the switching frequency and the number of paths, so that in the present example the residual ripple frequency is twice the switching frequency. This frequency multiplication combined with the low residual ripple amplitude at the output terminal 82 means that the output capacitor 86 can have much lower capacitance and ripple current rating then for a conventional supply circuit. In some applications of the present circuit, the output capacitor 86 may not be required for ripple reduction at all.

The values of the resistors 90 and 88 of the inductor-resistor combinations are chosen to balance the d.c. currents supplied to the terminal 82 through the inductors 89 and 87. In a similar circuit using more than two controlled switches, the resistors of the respective inductor-resistor combinations can in the same way be chosen to achieve equality of the magnitudes of the individual currents passed through the respective inductors and the associated controlled switches.

Figure 15:
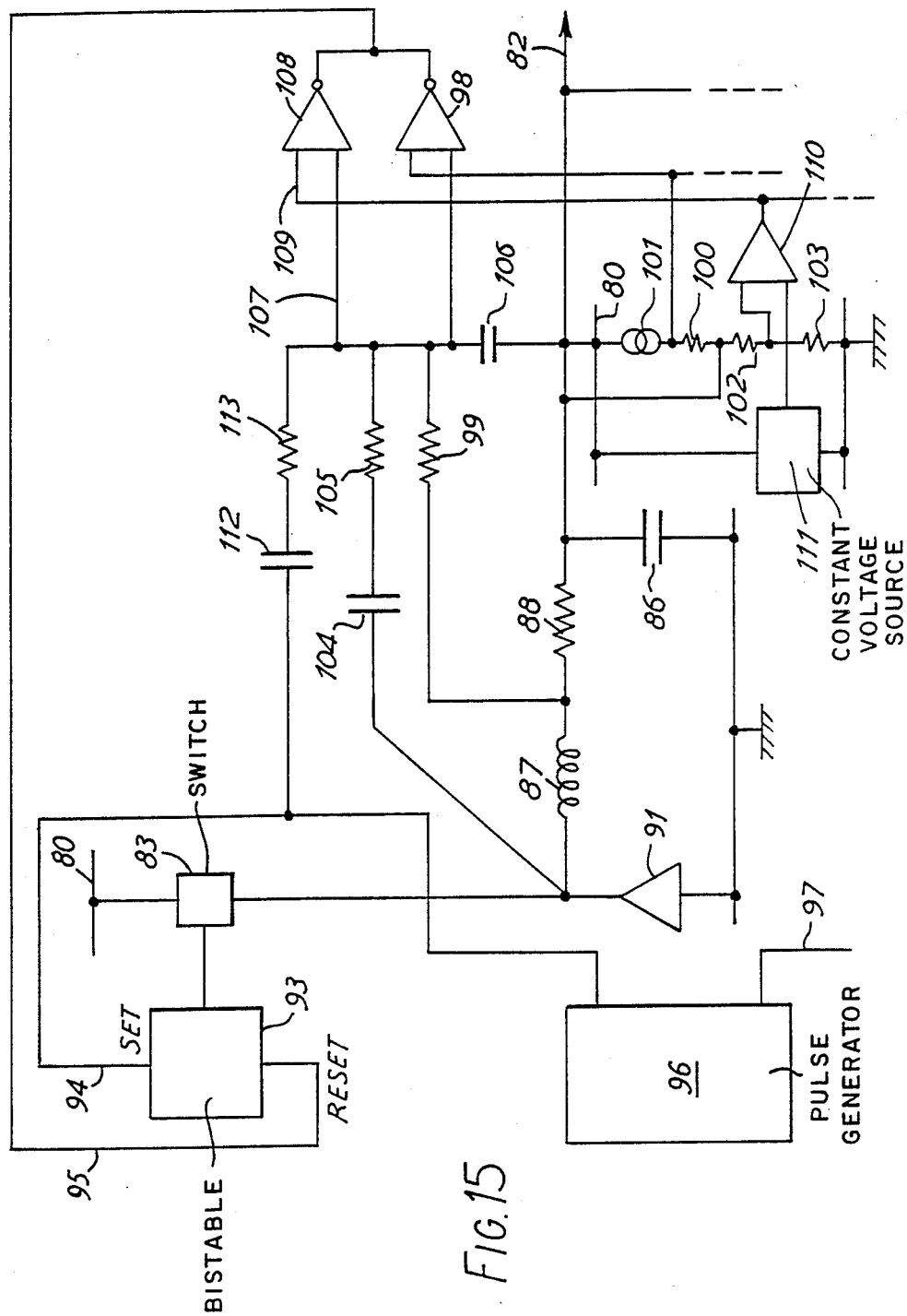
FIG. 15 is a more detailed circuit diagram of part of a power supply similar to that of FIG. 14.

FIG. 15 illustrates in more detail the control and feedback elements of a circuit similar to the circuit of FIG. 14 and shows corresponding components with the same reference numerals.

The state of the switch 83 is determined by the output from a bistable circuit 93. The switch 83 conducts whenever the bistable circuit 93 is in its SET state, and is non-conducting whenever the bistable circuit 93 is in its RESET state. The bistable circuit 93 is set by the low level of a negative-going set pulse on a SET line 94, and is reset by the low level of a negative-going reset pulse on a RESET line 95. If simultaneous low levels occur on the SET and RESET lines 94 and 95, the low level on the RESET line 95 prevails.

Set pulses are generated by a crystal-controlled set pulse generator 96 which generates two supplies of set pulses, the two supplies being 180° out of phase with one another. The SET line 94 applies the zero phase set pulses to the bistable circuit 93, and another SET line 97 supplies the 180° phase set pulses to another bistable circuit (not shown) which controls the state of the switch 84.

The reset pulses for the bistable circuit 93 are generated by feedback circuitry which senses the residual output ripple.

The mark/space ratio of the set pulses is 1:9 and their rate is 200 kilohertz, these pulses being generated in the generator 96 by division by ten of a 2 megahertz crystal clock oscillator output. Phase separation on the generator 96 can be obtained by taking different outputs from a divide-by-ten counter-divider circuit such as type 74HC4017.

The mark/space ratio of the reset pulses is variable and the timing of the leading and trailing edges of these pulses varies accordingly, thereby controlling the duration of the state of conduction of the switch 83 and hence the magnitude of the current passed thereby to the output terminal 82.

One form of control in dependence upon the ripple sensed in the current supplied to the terminal 82 by the switch 83 is effected through a voltage comparator 98 having one input terminal coupled through a resistor 99 to the inductor-end of the resistor 88, and the other input terminal coupled through a constant voltage drop resistor 100 to the terminal 82. A constant voltage drop of about +1 volt is provided across the resistor 100 by current from a constant current source 101 connected to the 30 volt supply rail 80 and to the resistor 100. Two further resistors 102 and 103 are connected in series between the output terminal 82 and ground. The source 101 is preferably a 4.7 milliamp Siliconix current diode. With this arrangement, the differential voltage input to the comparator 98 accurately follows the voltage variation across the resistor 88 and thus follows the variation in current. To sense the current ripple, a series combination of a capacitor 104, resistor 105 and capacitor 106 is connected across the combination of the inductor 87 and resistor 88. The ripple appears as a voltage across the capacitor 106 and is then applied to the comparator 98 and to a second comparator 108. The purpose of the resistor 88 is to sense a d.c. voltage proportional to the current through that resistor, which allows the currents in the two halves of the supply circuit to be balanced, and also allows current limiting.

The summing junction at one side of the capacitor 106 is also connected to one input terminal 107 of the voltage comparator 108. The other input terminal 109 of the comparator 108 is connected to the output terminal of a high-gain, inverting operational amplifier 110 having two inputs, one being a constant voltage relative to ground from a constant source 111, and the other the variable voltage which appears at the junction of the resistors 102 and 103. As a result, the voltage between the input terminals 107 and 109 of the comparator 108 is the difference between a substantially constant voltage $V_c$ at terminal 109 and the sum of the current ripple voltage $V_R$ and a slope correction voltage $V_{SC}$ obtained by integration of the set pulses through a capacitor-resistor coupling 113, 106 connected to the set pulse line 94 by a d.c. blocking capacitor 112. This sum voltage, $V_{FB}$, exceeds the substantially constant voltage $V_C$ over part of a 5 microsecond period, that part corresponding to output of a reset pulse by the comparator 108.

Figure 16:
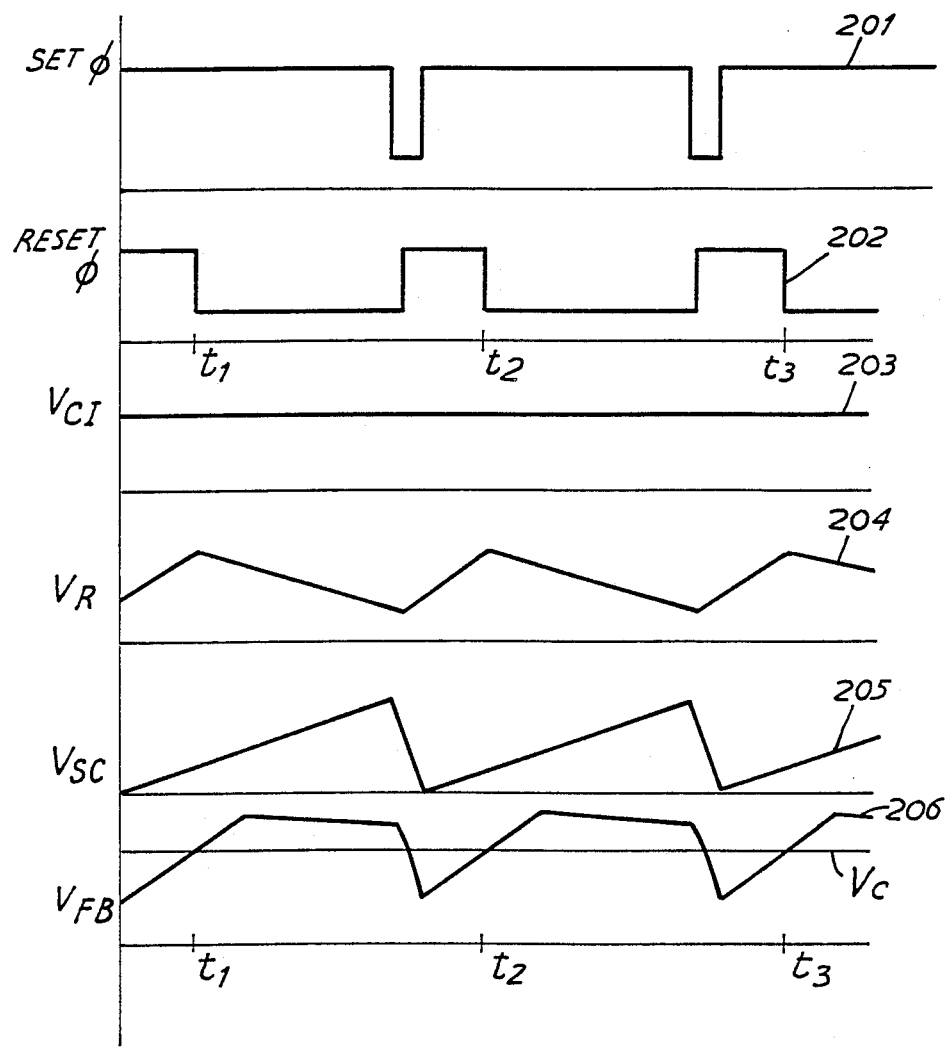
FIG. 16 is a graphical representation of waveforms appearing in the circuit of FIG. 15.

FIG. 16 shows six voltage waveforms 201 to 206 which are useful in explaining the operations of the circuit of FIG. 15. The time scales and relative timing are the same for each of these waveforms as illustrated. Waveform 201 is the zero phase set pulse waveform at the SET line 94, and waveform 202 is the reset pulse waveform at the RESET line 95. The waveform 203, designated $V_{CI}$ in FIG. 16, is the voltage level at the input terminal of the comparator 98 connected to the constant voltage resistor 100 and shows the sum of the voltage at the output terminal 82 and the voltage across the resistor 100 relative to ground. This voltage level $V_{CI}$ is substantially constant.

The waveform 204 is the ripple voltage $V_R$ which is supplied to terminal 107, and the waveform 205 is the slope control voltage $V_{SC}$ which is supplied to the terminal 107 by the integrating action of the coupling 113, 106 on the set pulses on line 94. The sum of these two waveforms 204 and 205 is the waveform 206 which represents the voltage $V_{FB}$ at the terminal 107, which is compared with the substantially constant voltage $V_C$ at the terminal 109. The slope control voltage $V_{SC}$ prevents subharmonics of the set pulse rate being generated by the feedback circuitry and interfering with the proper generation of reset pulses.

The value of the substantially constant voltage $V_C$ follows variation in the d.c. voltage level at the terminal 82 very closely and with high amplification, by virtue of the amplifier 110. Consequently, the times of occurence of the leading edges of the reset pulses, e.g. times $t_1$, $t_2$, $t_3$ in FIG. 16, vary with the d.c. voltage variations at the output terminal 82.

If the voltage $V_{FB}$ exceeds the voltage $V_{CI}$, the level at the RESET line 95 is held low, so that the output from the voltage comparator 98 is similar to that from the comparator 108. However, it is arranged that if the average level of current through the output terminal 82 rises above a predetermined value, the pulses generated by the comparator 98 mask those from the comparator 108 and rapidly reduce the conduction time of the switch 83 if the output current level at terminal 82 rises. At lower average output current levels, the pulses generated by the comparator 108 mask those generated by the comparator 98 and control of the reset pulse timing and duration is determined by the inputs to the comparator 108.

The example of FIG. 16 shows a condition in which the output current is slightly higher than a predetermined set point for control by the comparator 108, and accordingly the conduction time of the switch 83 is shorter than its non-conducting time.

The circuitry and method of control for the switch 84 duplicates that described hereinbefore for the switch 83, and items 96, 82, 100, 101, 102, 103, 110 and 111 are common to the circuitry for controlling the switches 83 and 84. For supply circuits similar to those of FIGS. 14 and 15 but having more than two current switches controlled in the same way as the switches 83 and 84, only the set pulse generator 96 need be modified to generate the necessary phases of set pulses. The concept of multiple switching paths disclosed herein can be applied to other power switching topologies, such as flyback circuitry, with similar advantages.

The video data circuitry of FIGS. 12 and 13 and the power supply circuitry of FIGS. 14 and 15 can be used in contexts other than an environmental control system, and need not be limited to the particular examples of such circuitry which are described and illustrated herein, and, of course, need not both be used in the same context.

Figure 17:
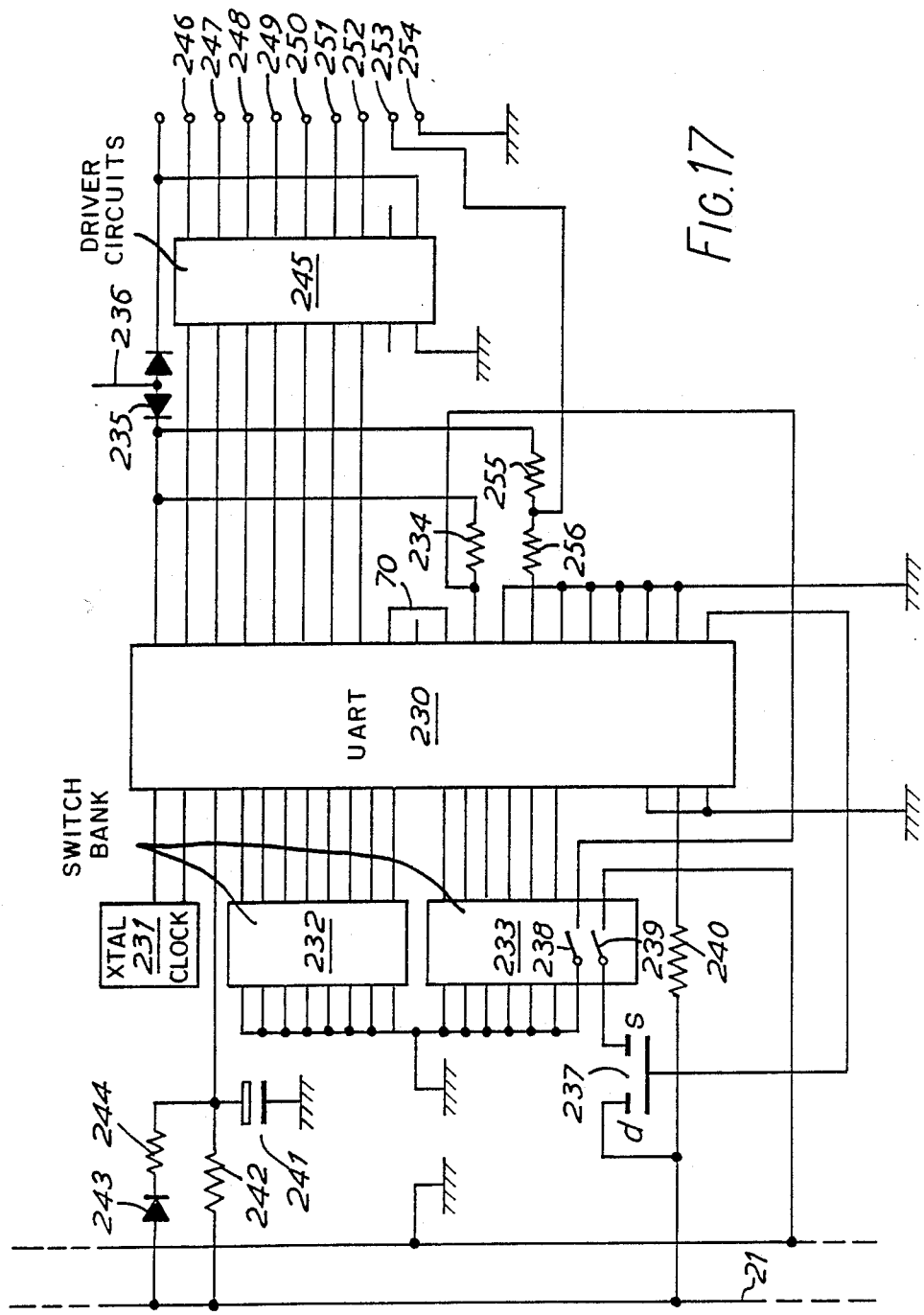
FIG. 17 is a circuit diagram of part of a controlled switching device of the apparatus of FIG. 1.

FIG. 17 is a circuit diagram of part of a switching device 22 and shows its UART 230 connected to the serial bus 21. In this example the control unit 17 and the switching device 22 communicate in half-duplex mode. The UART 230 is driven by a crystal-controlled clock 231. As a particular example, the UART 230 is an MC 14469 and the clock frequency is 307.2 kilohertz. The circuitry includes two banks 232,233 of eight manually settable single pole switches. One bank 232 has one side of all of its switches grounded and the other side connected to respective input pins of the UART 230, which in the example chosen are pins 4 to 11. The other bank 233 has one side of seven of its switches grounded, the other side of six of these seven connected to respective pins, input pins 12 to 17, of the UART 230, the other side of the seventh grounded switch 238 connected to one end of a resistor 234 coupled through a protective diode 235 to the positive supply line 236, and the eighth switch 239 connected in the source lead of a field effect transistor (FET) 237 used as a transponder switch by the UART 230. The drain lead of the FET 237 is connected directly to the serial bus 21, and its gate lead is connected to the serial output pin of the UART 230, which in the example is pin 21. The switch 239 must be closed for the transponder FET 237 to be operable. In the diagram of FIG. 17, pins 1 to 20 of the UART example, MC 14469, are represented at the left hand side of block 230 as viewed, with pin 1 at the top and pin 20 at the bottom, and pins 21 to 40 are represented at the right hand side of block 230 as viewed, with pin 21 at the bottom and pin 40 at the top. Pins 21, 22, 23, 24, 25 and 27, and pins 18 and 20, are grounded. Pin 19 is the serial input pin of the UART and is coupled by a resistor 240 to the serial bus 21. A reset signal at power up is coupled to the reset pin, pin 3, from a 10 Farad capacitor 241 which is normally held charged to the level of an enabling signal for the UART by a parallel combination of a 10 megohm resistor 242 and a diode 243 in series with a 220 kilohm resistor 244.

Figure 18:
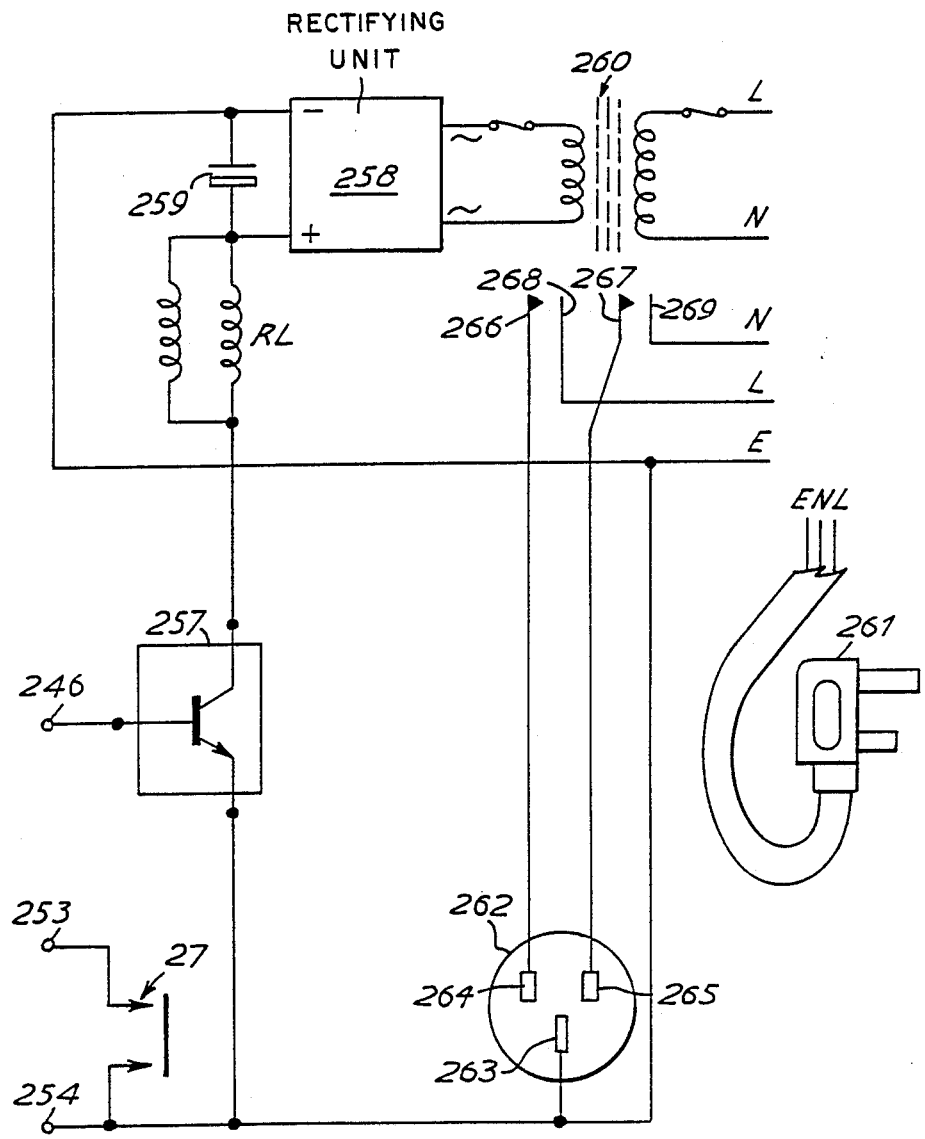
FIG. 18 is a circuit diagram of a further part of the controlled switching device of FIG. 17.

Seven parallel output pins, pins 33 to 39, of the UART 230 are connected to seven driver circuits in a bank of eight driver circuits provided, in this example, in the form of an integrated circuit 245, type ULN 2804A. The outputs of these seven driver circuits are connected respectively to seven relay control circuit terminals 246 to 252. The UART 230 can thus control up to seven relays. The relay control circuit connected to the terminal 246 is the control circuit of the relay used to control mains power supply to the appliance controlled by the switching device 22 incorporating the circuit of FIG. 17. If this appliance has other controlled functions, the relays controlling these functions are controlled by respective relay control circuits connected to one or more of the terminals 247 to 252. FIG. 18 shows the relay control circuit and relay circuit connected to the terminal 246. Two further terminals, 253 and 254, are part of the circuit of FIG. 18 and are connected to the fixed contacts of the push button switch 27. Operation of the push button switch 27 completes a connection between the terminals 253 and 254, thereby grounding a node between two series resistors 255, 256 coupling the diode 235 to another parallel input pin, pin 27, of the UART 230. Hence the UART 230 is able to sense momentary closure of the push button switch 27.

As shown in FIG. 18, the terminal 246 is connected to the control electrode, in this example the gate, of controlled switch 257. The power electrodes, here the collector and emitter, of the switch 257 are connected to one end of the coils of a relay RL and to the ground terminal 254 respectively. Power for the relay RL and the switch 257 is provided by a rectifying unit 258 having an output smoothing capacitor 259 and receiving a low voltage a.c. mains frequency input from a step down transformer 260 having its primary connected between the live and neutral lines L and N of a domestic a.c. mains supply when a mains plug 261 of the circuit is inserted into an a.c. mains output socket (not shown) and the associated mains switch (not shown) turned on. The earth line E of the mains plug 261 is connected to the negative d.c. output terminal of the rectifier unit 258 and to the terminal 254.

A power output socket 262 provided to receive the mains power plug (not shown) of the controlled appliance (not shown) has an earth contact 263 connected to the earth line E, and two other contacts 264 and 265 which are respectively connected to two fixed contacts 266 and 267 of the relay RL. A moving relay contact 268 associated with the fixed contact 266 is connected to the live line L of the plug 261, and a moving relay contact 269 associated with the fixed contact 267 is connected to the neutral line N of the plug 261. The fixed and moving contacts 266 and 268 form one normally open pair of relay contacts, and the fixed and moving contacts 267 and 269 from another normally open pair of relay contacts. Whenever the coils of the relay RL are energised, the contact 264 of socket 262 is connected by the contacts 266 and 268 to the live pin of the plug 261, and the contact 265 of the socket 261 is connected by the contacts 267 and 269 to the neutral pin of the plug 261.

In use when the plug 261 is engaged in a socket (not shown) supplying mains power, and a controlled appliance has its plug (not shown) engaged in the socket 262, the supplying of power to the appliance is controlled by the state of the switch 257 as determined by the control signal applied to the terminal 246. The state of control, and hence that of the switch 257, can be changed by an able bodied attendant pressing the push button 27 momentarily.

If the push button 27 is pressed momentarily, the UART 230 changes the state of a status bit stored within the UART 230, so that the change indicates that actuation of the push button 27 has occurred. This status but is transmitted back to the control unit 17 at the next addressing of the UART 230 in the interrupt program described hereinbefore. Detection of "push button actuated" by the control unit 17 results in an appliance status bit in the control unit memory being toggled, i.e. being changed from 0 to 1 or from 1 to 0, for the appliance associated with the particular UART 230. The change of the appliance status bit results in a change in the status of the appliance as displayed on the screen 23 of the monitor 15 if active, or only in a corresponding screen memory, and a corresponding change in the state of the control signal applied to the control terminal 246. The interrupt program is also restarted from the interrogation of the switching device 22 with the actuated push button 27, and the resultant detection of "push button actuated" is ignored.

The control unit 17 detects "push button actuated" by comparing the state of the received status bit associated with the push button 27 with a memory bit which is an image of the received status bit received at the previous run of the interrupt. If the memory bit and the currently received bit are in the same state, i.e. both 0 or both 1, the push button 27 has not been actuated in the last 20 milliseconds. If the states of these two bits differ, then the the push button has been actuated in the last 20 milliseconds.

The identity of the UART 230, i.e., which switching device 22 associated with which input station 14 and what relays are controlled by the UART 230 is set by the states of the switches of the banks 232 and 233 connected to pins 4 to 17 and 29 of the UART 230. The resistor 234 coupling pin 29 to the positive supply line 236 through the diode 235 is necessary since the pin 29 has no internal pull up resistor.

Pins 30 and 32 of the UART 230 are connected together by a link 270 to ensure that the UART 230 automatically transmits back to the control unit 17 immediately after receiving an instruction from the control unit 17. Pin 30 of the particular UART 230 in the present example is the output terminal for a pulse generated by the UART when data from the control unit 17 is correctly received, and pin 32 is the input terminal for a pulse to trigger the sending of data back to the control unit 17.

What is claimed is:

1. An environmental control system for controlling electrically powered domestic equipment in a dwelling, the control system comprising:
   (1) a control unit;
   (2) a plurality of input stations each located in a different one of a plurality of rooms in said dwelling;
   (3) a plurality of electrically operable switching devices including a plurality of groups of said switching devices, each said group being located in a respective one of said rooms;
   (4) sensing and control channel means connecting the control unit to each of said switching devices;
   (5) communication channel means connecting the control unit to each of said input stations;
   each input station comprising:
   (i) visible screen display means;
   (ii) an input device; and
   (iii) station identity storage means storing a station identity code;
   each electrically operable switching device comprising:
   (i) plug means for electrically connecting the device to a domestic power supply socket;
   (ii) output power socket means;
   (iii) controllable switch means for interconnecting and disconnecting said plug means and said socket means; and
   (iv) switching device identity storage means storing a switching device identity code;
   said control unit being connected to each said visible display means, to each said input device, and to each said station identity storage means through said communication lines; and said control unit comprising data storage and processing means programmed to distinguish between said identity codes and to respond to solely a selected one of said input devices, said storage and processing means being further programmed:
   (a) to select as said one input device the first one of said input devices which is actuated after a predetermined length of time in which none of said input devices is actuated;
   (b) to supply display data through said communication channel means to the visible screen display means of solely that input station to which said selected input device belongs to display thereon information comprising status information relating to that one group of said switching devices which is located in the room containing said visible screen display means being supplied; and
   (c) to respond to actuation of said selected input device to control through said sensing and control channel means said one group of switching devices and to indicate such control by display at said visible screen display means being supplied.

2. A control system according to claim 1, wherein at least one of the switching devices includes manually operable means for signalling a request to the control unit to change a control state of the switching device, and the control unit includes means for sensing the request and for controlling the switching device as to effect the requested change.

3. A control system according to claim 2, wherein the control unit is coupled to the switching devices by a serial link, the manually operable means is in the form of a push button switch, and said storage and processing means is further programmed to supply display data through said communication channel means to said visible screen display means being supplied to indicate a change effected in response to said request.

4. A control system according to claim 1, wherein the control unit is coupled to the switching devices by a serial link, and the input stations are coupled to the control unit by the serial link.

5. A control system according to claim 1, wherein each visible screen display means comprises means for presenting a television-type raster.

* * * * *